United States Patent
Bedi

Patent Number: 5,664,946
Date of Patent: Sep. 9, 1997

[54] WEDGE

[75] Inventor: Raman Bedi, Birmingham, United Kingdom

[73] Assignee: The University of Birmingham, Birmingham, United Kingdom

[21] Appl. No.: 507,375

[22] PCT Filed: Feb. 16, 1994

[86] PCT No.: PCT/GB94/00308

§ 371 Date: Oct. 12, 1995

§ 102(e) Date: Oct. 12, 1995

[87] PCT Pub. No.: WO94/18902

PCT Pub. Date: Sep. 1, 1994

[30] Foreign Application Priority Data

Feb. 20, 1993 [GB] United Kingdom ............... 9303435

[51] Int. Cl.[6] ............................................. A61C 5/00
[52] U.S. Cl. ................................ 433/140; 600/238
[58] Field of Search .......................... 433/93, 136, 140; 600/237, 238, 239, 243; 606/234, 235, 236

[56] References Cited

U.S. PATENT DOCUMENTS

| 307,930 | 11/1884 | Ehrhardt . | |
| 1,657,148 | 1/1928 | Catlin | 600/237 |
| 2,220,674 | 11/1940 | Bloomheart | 600/238 |
| 3,352,301 | 11/1967 | Abelson | 128/859 |
| 3,825,014 | 7/1974 | Wroten | 606/236 |
| 4,585,416 | 4/1986 | DeNiro et al. | 433/140 |
| 4,944,313 | 7/1990 | Katz et al. . | |
| 5,275,619 | 1/1994 | Engebretson et al. | 606/236 |

FOREIGN PATENT DOCUMENTS

| 196552 | 4/1923 | United Kingdom | 600/238 |

*Primary Examiner*—Cary E. O'Connor
*Attorney, Agent, or Firm*—Jacobson, Price, Holman & Stern, PLLC

[57] ABSTRACT

A dental wedge for propping open the mount of a patient to facilitate oral examination and treatment has an elongate portion which in use, is inserted between the jaws of a patient. The wedge further has a pair of oppositely directed flanges extended laterally from the elongate portion at or near the distal end of the latter. The flanges serve to limit insertion of the elongate portion into the mouth of the patient. The elongate portion is hollow to enable insertion of a finger of the person carrying out examination and treatment.

7 Claims, 2 Drawing Sheets

WEDGE

BACKGROUND OF THE INVENTION

This invention relates to a wedge and is more particularly concerned with a wedge for propping open the mouth of a patient (human or animal) in order to facilitate oral examination and/or treatment, eg dental treatment or cleaning of the teeth. Oral examination or treatment on uncooperative patients and especially those with special needs, is usually effected by wedging open the mouth of the patient with a finger or by using a mouth gag or prop, and by restraining head movement. However, there are dangers inherent to this procedure and it is an object of the present invention to provide a dental wedge which can enable oral examination and/or treatment to be carried out more safely both for the patient and for the person carrying out such examination and/or treatment.

SUMMARY OF THE INVENTION

According to one aspect of the present invention, there is provided a dental wedge comprising an elongate portion which is adapted to be inserted between the jaws of the patient, and at least one flange extending laterally from the elongate portion at or near the distal end of the latter, said at least one flange serving to limit insertion of the elongate portion into the mouth of the patient.

Preferably, the elongate portion is capable of elastic deformation, whereby to reduce damage to the patient. Preferably, two oppositely directed flanges are provided. Said at least one flange is preferably dimensioned so that the wedge cannot be swallowed or inhaled. The flange or flanges are preferably integrally formed with the elongate portion. The elongate portion may be hollow and of a size to receive a finger of the person carrying out the examination and/or treatment. Such hollow elongate portion may have a substantially oval cross-section to provide an improved grip on the finger. One or more passages and/or grooves may be provided in or through said at least one flange portion and/or said elongate portion in order to facilitate breathing of the patient.

In a convenient embodiment, the wedge is provided with a handle whereby it can be held between the fingers rather than supported between the jaws of the patient by insertion of the finger into the elongate portion.

Other possible modifications include forming the elongate portion so that it includes means for performing additional dental functions including tongue depression and liquid aspiration.

The elongate portion may have undulations or other formation thereon to resist slippage from between the jaws of the patent in use.

Also according to the present invention, there is provided a method of propping open the mouth of a patient, comprising inserting between the jaws of the patient a wedge according to the present invention.

Embodiments of the present invention will now be described, by way of example, with reference to the accompanying drawings, in which:

DESCRIPTION OF PREFERRED EMBODIMENTS

Figure 1:
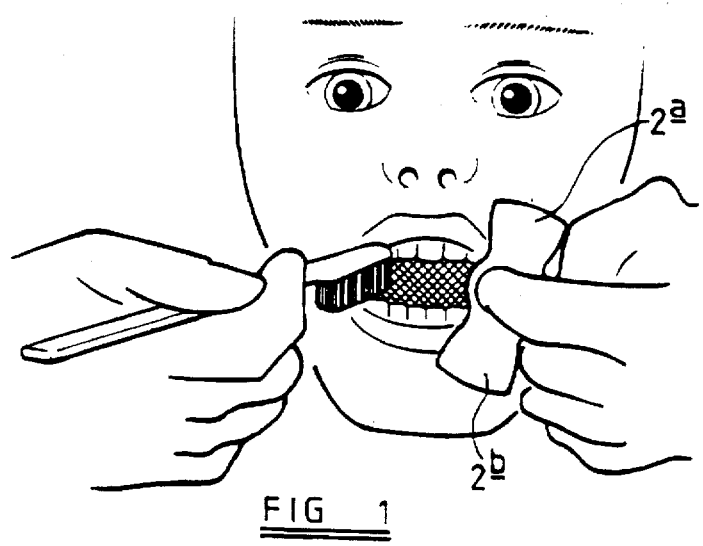
FIG. 1 shows the use of a dental wedge according to the present invention.
Figure 4:
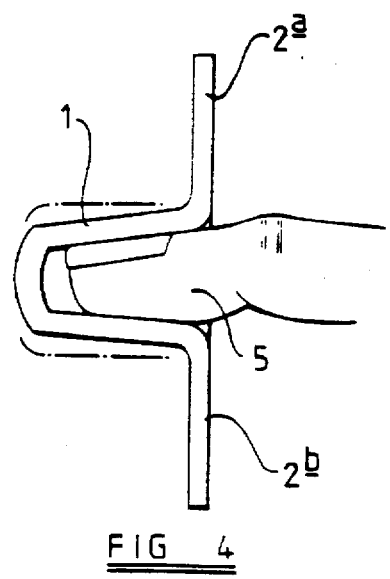

In FIG. 1, a dental wedge similar to that illustrated in FIG. 4 is inserted between the jaws of a patient to allow teeth to be cleaned.

Figure 2:
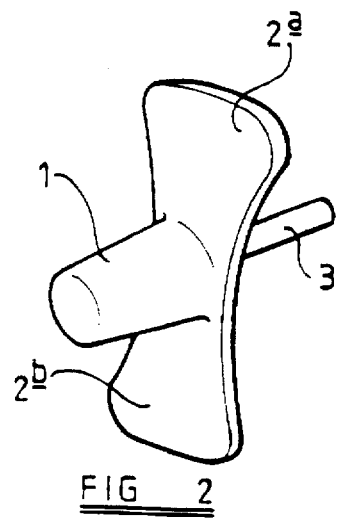
FIGS. 2 to 8 show various forms of the device.

In FIG. 2, the wedge comprises a frusto-conically tapered elongate portion in the form of rod 1 with integrally moulded, oppositely directed flanges 2a and 2b at the base distal end of the rod 1, and a handle 3 extending substantially coaxially with the rod 1 in the opposite direction away from flanges 2a and 2b. The device is moulded from a suitably strong, resilient, inert plastics material such as Kel-F (EX3M Company). In use, rod 1 is inserted using the handle 3 and the rod 1 between the patient's jaws until the flanges 2a and 2b abut against the face of the patient so as to assist in locating the rod 1 between the teeth and preventing the wedge from being swallowed or being inhaled.

Figure 3:
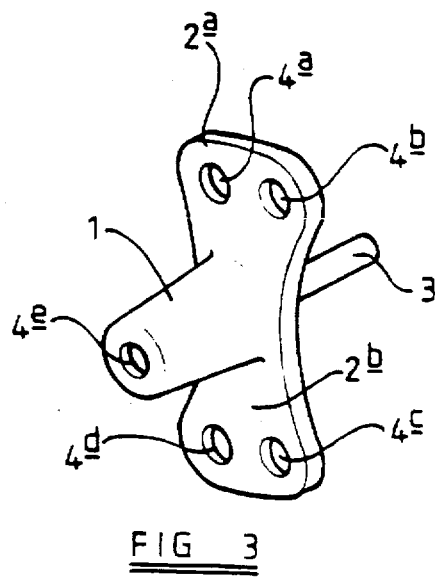

In FIG. 3, passages 4a to 4e are provided in the flanges 2a and 2b and rod 1 so as to prevent the patient's breathing from being unduly impaired in the unlikely event that the whole of the wedge enters the mouth.

In FIG. 4, the rod 1 is hollow so as to accept a finger 5 for positioning the device instead of using handle 3 as in the embodiments of FIGS. 2 and 3. The resilience of the hollow rod 1 allows the biting force to be sensed and thereby the response of the patient to treatment to be assessed. The hollow within the rod 1 is of frusto-conical form in order to accommodate different finger sizes. Alternatively, the hollow in the rod 1 may be stepped also to accommodate different finger sizes. The outside of the rod 1 may follow the frusto-conical form of the hollow, or be of uniform diameter or indeed slope conically towards the flanges 2a and 2b to help prevent the biting force from ejecting the wedge.

Figure 5:
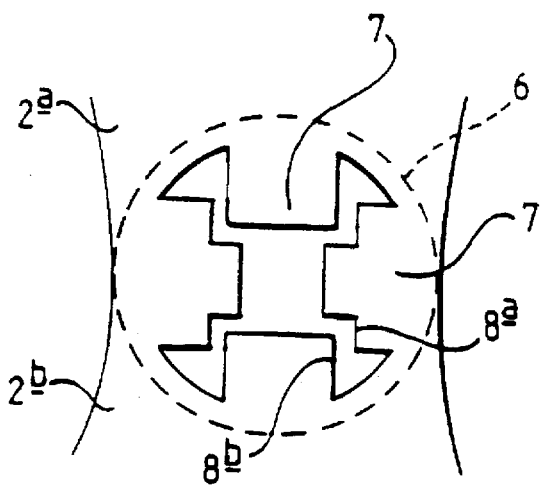

In FIG. 5, the hollow within the rod 1 is provided internally with stops 7 including abutments 8a and 8b which can mutually engage to prevent excessive biting force being applied to a finger inserted into the hollow in the rod. The rod 1 in the region of the stops 7 is relatively rigid, whilst it is elastically deformable in the region of portions 6.

Figure 6:
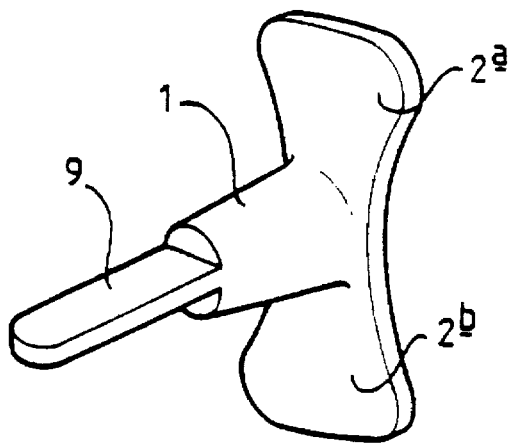

In FIG. 6, the rod 1 is integrally formed at its distal end with a spatula 9 which is used to restrict movement of the tongue of the patient.

Figure 7:
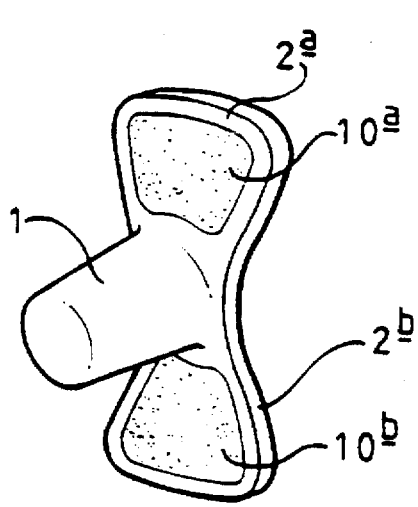

In FIG. 7, the flanges 2a and 2b are shown with respective adhesive pads 10a and 10b by means of which the wedge can be secured temporarily against the face of the patient so as to leave both hands free for examination and/or treatment.

Figure 8:
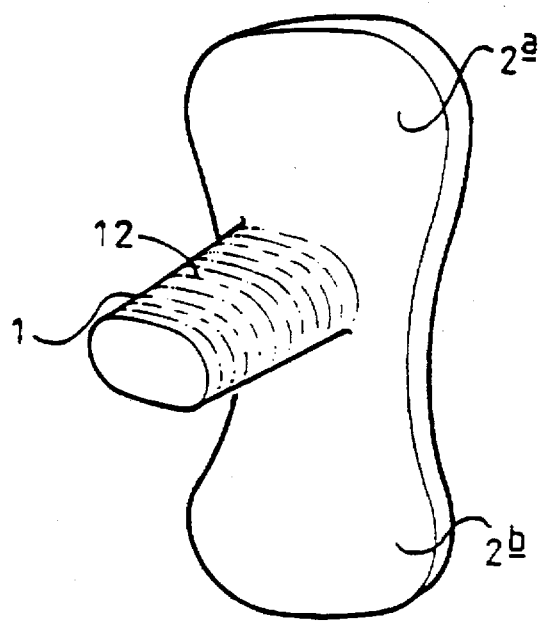

In FIG. 8, the hollow rod 1 is of substantially oval cross-section rather than circular as in the previous embodiments, so as to provide a better grip on the finger of the user. Additionally, the outer peripheral surface of the rod 1 has undulations 12 thereon to resist slippage in use from between the jaws of the patient.

In modifications (not shown) instead of using adhesive pads, any other means such as one or more clips, straps or even suction may be employed to secure the wedge in position temporarily during examination and/or treatment.

It will be seen that, in all of the above embodiments, the flanges 2a and 2b are essentially planar with a width which increases outwardly from the rod 1. Thus, the flanges 2a and 2b have a limited width in the region of the rod 1. This provides minimum obscuring of the mouth.

I claim:

1. A dental wedge for use as a prop between a patient's jaws during dental work comprising a hollow elongate portion having a longitudinal axis, a blunt proximal end and a distal end, said proximal end being closed, and said distal end being open said elongate portion tapering from a larger cross-sectional area at said distal end to a smaller cross-sectional area at said proximal end and defining a receptacle having a size so that a finger of an operator can be inserted into said hollow elongate portion through said open distal end to enable manipulation of the wedge in the mouth of a patient, and said dental wedge also comprising a pair of oppositely-directed flanges which project laterally of said hollow elongate portion and which are disposed adjacent said open distal end, said oppositely-directed flanges having opposed major surfaces substantially perpendicular to said axis, said flanges being arranged to abut against a face of the patient so as to assist in locating said hollow elongate portion between the teeth and preventing the wedge from been swallowed.

2. A dental wedge as claimed in claim 1, wherein the elongate portion comprises a material which is capable of elastic deformation.

3. A dental wedge as claimed in claim 1, wherein the elongate portion has a substantially oval cross-section.

4. A dental wedge as claimed in claim 1, wherein at least one passage is provided in at least one of said flanges in order to facilitate breathing of the patient.

5. A dental wedge as claimed in claim 1, further including means for performing additional dental functions.

6. A dental wedge as claimed in claim 1, wherein the elongate portion has undulations thereon to resist slippage from between the jaws of the patient in use.

7. A method of propping open the mount of a patient comprising inserting between the jaws of the patient a dental wedge as claimed in claim 1.

* * * * *